(12) United States Patent
Wodlinger (10) Patent No.: US 10,492,763 B2
(45) Date of Patent: Dec. 3, 2019

(54) MEDICAL IMAGE PROCESSING SYSTEMS AND METHODS THEREOF

(71) Applicant: Exact Imaging Inc., Ontario (CA)

(72) Inventor: Brian C. Wodlinger, Ontario (CA)

(73) Assignee: Exact Imaging Inc. (CA)

( * ) Notice: Subject to any disclaimer, the term of this patent is extended or adjusted under 35 U.S.C. 154(b) by 439 days.

(21) Appl. No.: 15/305,841

(22) PCT Filed: Apr. 20, 2015

(86) PCT No.: PCT/IB2015/052882
§ 371 (c)(1),
(2) Date: Oct. 21, 2016

(87) PCT Pub. No.: WO2015/162543
PCT Pub. Date: Oct. 29, 2015

(65) Prior Publication Data
US 2017/0042514 A1    Feb. 16, 2017

Related U.S. Application Data

(60) Provisional application No. 61/983,033, filed on Apr. 23, 2014.

(51) Int. Cl.
*A61B 8/08* (2006.01)
*A61B 8/00* (2006.01)
(Continued)

(52) U.S. Cl.
CPC ............ *A61B 8/5269* (2013.01); *A61B 8/145* (2013.01); *A61B 8/4488* (2013.01);
(Continued)

(58) Field of Classification Search
CPC ..................... A61B 8/5269; A61B 8/5207
See application file for complete search history.

(56) References Cited

U.S. PATENT DOCUMENTS

| 4,654,795 A | 3/1987 | Shimoni |
| 7,492,947 B2 | 2/2009 | Nanbu |

(Continued)

FOREIGN PATENT DOCUMENTS

WO    WO 2007-110669 A1    10/2007

OTHER PUBLICATIONS

Abeyratne et al., "On Modeling the Tissue Response From Ultrasonic B-Scan Images", IEEE Transactions on Medical Imaging, Aug. 1996, 15(4), 479-490.

(Continued)

*Primary Examiner* — Tse W Chen
*Assistant Examiner* — Milton Truong
(74) *Attorney, Agent, or Firm* — BakerHostetler (57) ABSTRACT

The present invention provides improved medical imaging apparatuses, systems and methods, especially those using ultrasonography. For example, an imaging system can include a transducer, a scanner, a signal processing unit, and a display unit. The scanner, coupled to the transducer, can convert analog signals to a plurality of digital signals. The signal processing unit, coupled to the scanner, can be configured to: receive the plurality of digital signals; multiply a first magnitude estimate of the plurality of digital signals by a probability that an actual magnitude of the plurality of digital signals is greater than zero to determine a second magnitude; and form an image based on the second magnitude estimate. The display unit displays the image. The present invention also provides for products produced by the methods of the present invention and for apparatuses used to perform the methods of the present invention.

8 Claims, 8 Drawing Sheets

(51) Int. Cl.
*G01S 15/89* (2006.01)
*A61B 8/14* (2006.01)
*G01S 7/52* (2006.01)

(52) U.S. Cl.
CPC ............ *A61B 8/5207* (2013.01); *A61B 8/587* (2013.01); *G01S 7/52071* (2013.01); *G01S 15/8988* (2013.01)

(56) References Cited

U.S. PATENT DOCUMENTS

| | | | |
|---|---|---|---|
| 7,720,268 | B2 | 5/2010 | Slablaugh et al. |
| 8,194,937 | B2 | 6/2012 | Chen |
| 8,594,444 | B2 | 11/2013 | Geiger et al. |
| 8,824,762 | B2 | 9/2014 | Rivaz et al. |
| 9,610,061 | B2 | 4/2017 | Ebbini |
| 9,817,119 | B2 | 11/2017 | Kobayashi |
| 2013/0243296 | A1 | 9/2013 | Nandi et al. |
| 2014/0086014 | A1* | 3/2014 | Kobayashi .......... G01S 7/52066 367/90 |

OTHER PUBLICATIONS

Ali et al., "Signal Processing Overview of Ultrasound Systems for Medical Imaging", Texas Instruments White Paper, SPRAB12—Nov. 2008.

Cunningham et al., "Signal-to-noise Optimization of Medical Imaging Systems", Journal of the Optical Society of America A, Mar. 1999, 16(3), 621-632.

Eltoft, Torben, "Modeling the Amplitude Statistics of Ultrasonic Images", IEEE Transactions on Medical Imaging, Feb. 2006, 25(2), 229-240.

Evans et al., "Mode Filtering to Reduce Ultrasound Speckle for Feature Extraction", IEE Proceedings—Vision, Image and Signal Processing, Apr. 1995, 142(2), 87-94.

Kutay et al., "Power-Law Shot Noise Model for the Ultrasound RF Echo", IEEE International Conference on Acoustics, Speech, and Signal Processing, ICASSP'00, Jun. 2000, vol. 6, 3787-3790.

Tay et al., "Ultrasound Despeckling for Contrast Enhancement", IEEE Transactions on Image Processing, Jul. 2010, 19(7), 1847-1860.

* cited by examiner

Simplified Technique

FIG. 5B

Standard Technique

FIG. 5A

FIG. 6A Simple Average

FIG. 6B Simplified Technique

FIG. 6C Unbiased Technique

FIG. 6D Combined Technique

FIG. 7D Combined Technique

FIG. 7C Unbiased Technique

FIG. 7B Simplified Technique

FIG. 7A Simple Average

FIG. 8

MEDICAL IMAGE PROCESSING SYSTEMS AND METHODS THEREOF

CROSS-REFERENCE TO RELATED APPLICATIONS

This application is the National Stage of International Patent Application No. PCT/IB2015/052882, filed Apr. 20, 2015, which claims the benefit of US Provisional Patent Application No. 61/983,033, filed Apr. 23, 2014, the disclosures of which are incorporated herein by reference in their entireties.

FIELD OF THE INVENTION

The disclosed invention is in the field of medical image processing, particularly in medical ultrasonography.

BACKGROUND OF THE INVENTION

The standard ultrasound image, known as B-Mode (or Brightness Mode), is created using the magnitude of the radio frequency signal to control brightness of each pixel. For example, the magnitude estimate of each pixel is determined by an algorithm such as Euclidean-norm using quadrature and in-phase signals. However, because the quadrature and in-phase signals recorded are often corrupted by noise and taking the magnitude involves squaring these signals, the magnitude estimates become biased such that the estimate does not converge to the true value, especially as the number of observation becomes large. In other words, in low signal-to-noise ratio regions, when the quadrature and in-phase components are small, the magnitude estimate reaches a floor and simple averaging of the magnitude values gives no benefit. Moreover, the standard technique of averaging the quadrature and in-phase values before taking the magnitude is also ineffective in many cases due to phase variation from small movements, etc. If two quadrature and in-phase pair samples have the same magnitude but are rotated by 180 degrees, averaging the quadrature and in-phase values will cause them to cancel to zero. Accordingly, there is a need for image processing systems and methods that address these problems. The inventions disclosed herein are directed to these and other important needs.

SUMMARY OF THE INVENTION

The present invention provides imaging systems comprising: a transducer; a scanner, operatively connected to the transducer for converting a plurality of analog signals from the transducer to a plurality of digital signals; a signal processing unit operatively connected to the scanner, the signal processing unit configured to receive the plurality of digital signals, the plurality of digital signals being correlated to a magnitude of a pixel, multiply a first magnitude estimate of the plurality of digital signals by a probability that an actual magnitude of the plurality of digital signals is greater than 0 to determine a second magnitude estimate, and form an image based on the second magnitude estimate; and a display unit, connected to the signal processing unit, showing the image.

Also provided are methods for forming an image. The disclosed methods comprise receiving, at one or more processors, a plurality of digital signals, the plurality of digital signals being correlated to a magnitude of a pixel; multiplying, via the one or more processors, a first magnitude estimate of the plurality of digital signals by a probability that an actual magnitude of the plurality of digital signals is greater than 0 to determine a second magnitude estimate; and forming the image based on the second magnitude estimate.

Also provided are methods for forming an image, comprising: receiving, at one or more processors, a plurality of digital signals, the plurality of digital signals being correlated to a magnitude of a pixel; determining, via the one or more processors, a magnitude estimate using formula:

$$\hat{v} = \left(\frac{1}{N}\Sigma_i v_i\right)\left(1 - \frac{e^{\frac{1}{N}\Sigma_i -v_i^2/2\sigma^2}}{A}\right)$$

wherein, $\hat{v}$ is the magnitude estimate, N is a number of samples, $v_i$ is an $i^{th}$ input magnitude, $\sigma$ is a standard deviation of noise in Gaussian distribution, and A is a constant for a filter aggressiveness; and forming the image based on the magnitude estimate.

The present invention also provides a computer readable storage medium, comprising executable instructions that when executed by a process cause the processor to effectuate image processing operations comprising: receiving a plurality of digital signals, the plurality of digital signals being correlated to a magnitude of a pixel; multiplying a first magnitude estimate of the plurality of digital signals by a probability that an actual magnitude of the plurality of digital signals is greater than 0 to determine a second magnitude estimate; and forming an image based on the second magnitude estimate.

Also provided are imaging systems comprising: a transducer; a scanner, operatively connected to the transducer for converting a plurality of analog signals from the transducer to a plurality of digital signals; a signal processing unit, operatively connected to the scanner, the signal processing unit configured to: receive a plurality of digital signals, the plurality of digital signals being correlated to a magnitude of a pixel; determine a first magnitude estimate of the plurality of digital signals, the first magnitude estimate being indicative of a standard magnitude estimate; determine a second magnitude estimate by subtracting a standard deviation of noise from the first magnitude estimate; determine a third magnitude estimate by multiplying the first magnitude estimate and a probability that an actual magnitude of the plurality of digital signals is greater than 0; determine a fourth magnitude estimate by averaging the second magnitude estimate and the third magnitude estimate; compare error rates for true magnitude values in determining the second, third, and fourth magnitude estimates to select a reliable magnitude estimate; and form at least one portion of an image based upon the reliable magnitude estimate; and a display unit, connected to the signal processing unit, showing the image.

Also provided are methods for forming an image. The disclosed methods comprise receiving, at one or more processors, a plurality of digital signals, the plurality of digital signals being correlated to a magnitude of a pixel; determining, via the one or more processors, a first magnitude estimate of the plurality of digital signals, the first magnitude estimate being indicative of a standard magnitude estimate; determining, via the one or more processors, a second magnitude estimate by subtracting a standard deviation of noise from the first magnitude estimate; determining, via the one or more processors, a third magnitude estimate by multiplying the first magnitude estimate and a probability that an actual magnitude of the plurality of digital signals is greater than 0; determining, via the one or more processors, a fourth magnitude estimate by averaging the second magnitude estimate and the third magnitude estimate; compare error rates for true magnitude values in determining the second, third, and fourth magnitude estimates to select a reliable magnitude estimate; and form at least one portion of an image based upon the reliable magnitude estimate.

The general description and the following detailed description are exemplary and explanatory only and are not restrictive of the invention, as defined in the appended claims. Other aspects of the present invention will be apparent to those skilled in the art in view of the detailed description of the invention as provided herein.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIGS. 6 (A-D) provide ultrasound images illustrating the results of applying different magnitude estimate techniques to a HFUS phantom image;

FIGS. 7 (A-D) provide ultrasound images showing the results of applying different magnitude estimate techniques to a HFUS phantom image.

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, references to values stated in ranges include each and every value within that range.

Contrast resolution enhancement techniques (15) improves the contrast resolution in ultrasound images by taking a number of standard ultrasound (B-Mode) pixel values for the same pixel which have each been corrupted by noise and combining them to obtain a more accurate estimate of the true pixel value. The contrast resolution enhancement techniques (15) can be implemented with different magnitude estimate techniques such as the simplified, unbiased, and combined techniques. Disclosed herein are systems, methods, and devices for estimating of a signal whose components are corrupted by the presence of noise with the contrast resolution enhancement techniques (15).

Simplified Technique

Figure 1:
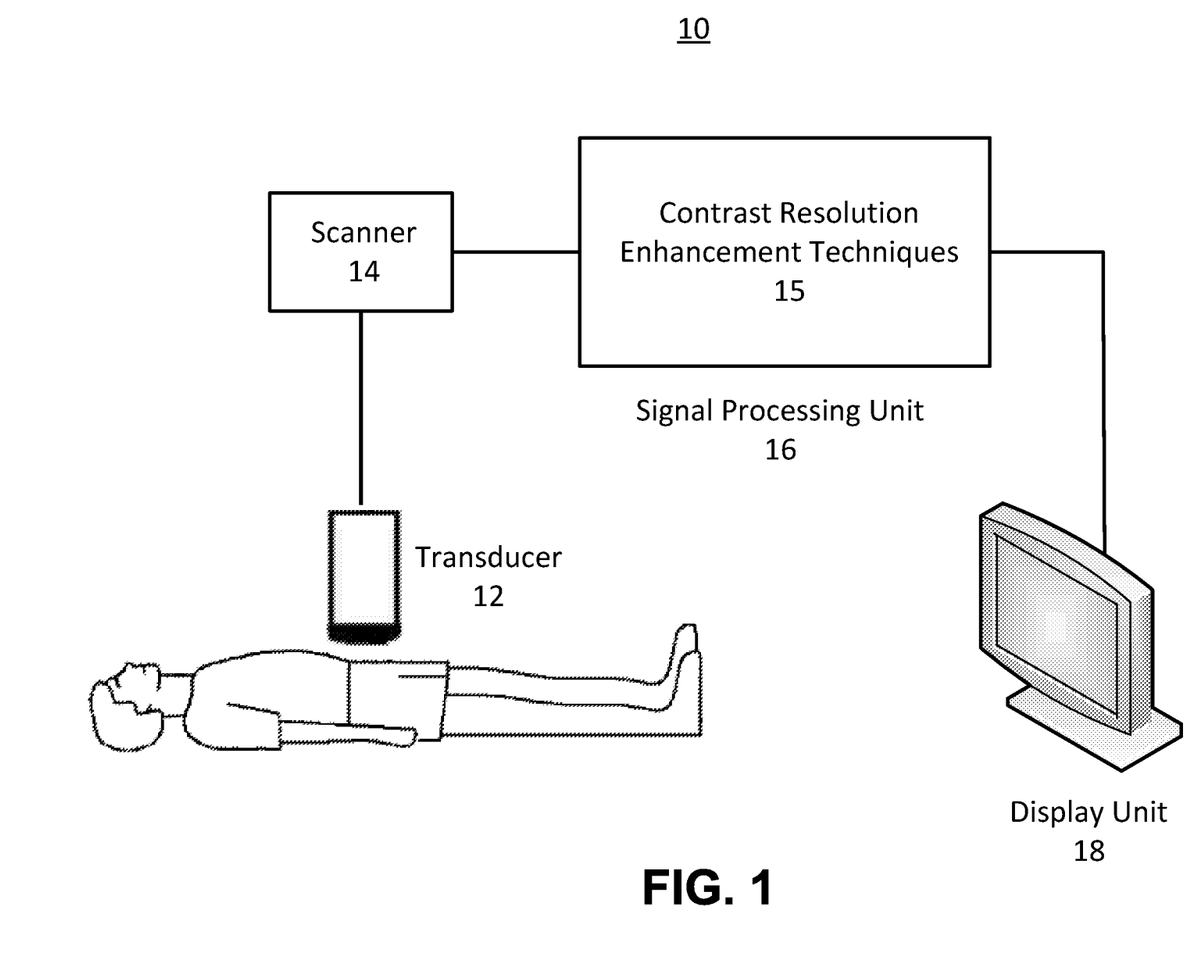
FIG. 1 illustrates a schematic diagram of an embodiment of the present invention directed to the imaging system (10) that estimates the magnitude of a signal whose components are corrupted by the presence of noise.

FIG. 1 illustrates an embodiment of imaging system (10) that estimates the magnitude of a signal whose components are corrupted by the presence of noise. The imaging system (10) can be directed to a simplified technique that enhances the contrast resolution of the ultrasound image. For example, the imaging system (10) includes a transducer (12), a scanner (14), a signal processing unit (16), and a display unit (18). The scanner (14), operatively connected to the transducer (12), can convert a plurality of analog signals received from the transducer (12) into a plurality of digital signals with standard signal acquisition techniques such as Quadrature sampling, Nyquist sampling, or the like. The signal processing unit (16), operatively connected to the scanner (14), can be configured to receive the plurality of digital signals from the scanner (14) to estimate the magnitude of the plurality of digital signals. The plurality of digital signals is being correlated to a magnitude of a pixel. By multiplying a first magnitude estimate of the plurality of digital signals and a probability that an actual magnitude of the plurality of digital signals is greater than zero, the signal processing unit (16) can determine a second magnitude estimate that provides improved contrast resolution in ultrasound images. The first magnitude estimate can be determined by taking the arithmetic mean of several input magnitudes that are calculated by algorithms such as Euclidean-norm, Hilbert transform, envelope detection, demodulation, or the like. The signal processing unit (16) can form an ultrasound image based upon the second magnitude estimate. The display unit (18), connected to the signal processing unit (16), can display the ultrasound image. The ultrasound image formed based on the second magnitude estimate has improved contrast resolution compared to the standard ultrasound image such as the B-Mode image.

The transducer (12) can include a transmitter and receiver module such as piezoelectric materials with electrodes on the top or bottom. With the transmitter and receiver module, the transducer (12) can emit ultrasound signals into a subject and receive the reflective signals from the subject. More specifically, the transmitter module can send out acoustic signals for each electrical excitation. When the receiver module resonates, they have a distinctive electrical impedance signature that can be measured electrically. In addition, the transducer (12) can appear in a wide variety of types. For example, the types of the transducer (12) can be a linear array, a convex array, a phased array, a transesophageal probe mounted on the end of a gastroscope, a stand-alone CW Doppler two-element transducer, a motorized transthoracic array with an internal motor drive for 3D acquisition, an intraoperative probe, or the like. The types of the transducer (12) are not limited to the specific types listed herein and can have any other types.

The scanner (14) in the imaging system (10) can perform beamforming and signal processing. For example, the scanner (14) provides functions of organizing many signals of the elements into coherent timelines of echoes for creating each line in the image. The transmit beamformer can send pulses to the elements on the transducer (12). Reflective signals can pass through an analog-to-digital (A/D) converter for digital beamforming. Moreover, the scanner (14) can also carry out signal processings, including filtering, creation of quadrature signals, and different modes such as Doppler and color flow.

The signal processing unit (16) can comprise one or more processors such as signal processors, preprocessors, post-processors or the like. The signal processing unit (16) can also perform image formation, display, image metrics, or the like. The signal processing unit (16) can receive, as an input, a set of pulse-echo envelope lines formed from each beam-formed radio frequency data line. Image formation can be achieved by organizing the lines and putting the lines though a digital scan converter that transforms them into a raster scan format for display on the display unit (18) such as video or PC monitor. The signal processing unit (16) can also perform appropriate preprocessing and post-processing, log compression, and color or gray-scale mapping. Image overlays containing alpha-numeric characters and other information can be added in image planes. The signal processing unit (16) can also perform various metric programs, such as measuring the length of a fetal femur, calculating areas, or performing videodensitometry. The one or more processors of the signal processing unit (16) can also be implemented by microprocessors.

As described above, the signal processing unit (16) can receive a plurality of digital signals converted from the scanner (14). The plurality of digital signals can be generated by standard signal acquisition techniques such as Quadrature sampling, Nyquist sampling, or the like. These techniques can produce slightly different signals each of which can be more suited to different algorithms to determine input magnitudes and estimate the magnitude of the plurality of digital signals. The different algorithms can include Euclidean-norm, Hilbert transform, envelope detection, demodulation or the like. For example, the Quadrature sampling can produce a plurality of digital signals with complex values at half the rate, while the plurality of digital signals produced by the Nyquist sampling are faster but real. More specifically, the Nyquist sampling can produce the plurality of digital signals at a rate of at least twice a frequency of a highest frequency component of received analog signals. The Quadrature sampling can produce the plurality of digital signals with complex values at least a half rate that the Nyquist sampling produces the plurality of digital signals. The sample rates in the Quadrature sampling, the Nyquist sampling, or the like can be changed depending on implementing techniques. The types of signal acquisition technique generating the plurality of digital signals are not limited to only those as listed herein and can be any type of signal acquisition technique.

The plurality of digital signals can have reflected signals (or echo signals) and corrupted signals by the presence of noise. Theses reflected signals come with different amplitudes and phases. This gives rise to an interference pattern known as noise. Noise is defined as unwanted random signal or unwanted data that may reduce the contrast, deteriorating the shape or size of objects in the image and blurring of edges or dilution of fine details in the image. Noise can be modeled mathematically. For example, additive noise known as Gaussian noise is statistical noise that has the probability density function same as that of the normal distribution, which is also known as Gaussian distribution. In other words, the values that the noise can take on are Gaussian-distributed. A person skilled in the art will understand that the calculations based on the Gaussian distribution apply equally to other continuous noise distributions with which a person skilled in the art will be familiar, and examples of which include $1/f\hat{\ }a$ or shot noise. A special case is white Gaussian noise, in which the values at any pairs of times are identically distributed and statistically independent (and hence uncorrelated). In applications, Gaussian noise is most commonly used as additive white noise to yield additive white Gaussian noise.

Assuming that the plurality of digital signals received from the scanner (14) has quadrature components and in-phase components and these components are corrupted by the white Gaussian noise, a magnitude image can be formed by calculating the magnitude, pixel by pixel, from the quadrature and in-phase components. The pixel by pixel magnitudes can be calculated by several other formulas such as Euclidean-norm, Hilbert transform, envelope detection, demodulation, or the like.

In the imaging system (10) for estimating the magnitude of the plurality of digital signals whose components are corrupted by the white Gaussian noise, or equivalent noise that can be approximated as white Gaussian noise for these purposes, for example, some non-white or non-Gaussian type noise may be modeled as white Gaussian noise with a given or acceptable error limit. The signal processing unit (16) can take a number of standard B-Mode ultrasound pixel values for the same pixel which have each been corrupted by the noise and combine them to achieve a more accurate estimate of the true pixel value. The standard B-Mode ultrasound pixel values can be referred to as brightness or magnitude. The sources of noise can be electrical noise in the amplifiers and signal paths, biological noise in the sample, or the like and are not limited to the sources listed herein.

As describe above, the algorithms such as Euclidean-norm, Hilbert transform, envelope detection, demodulation, or the like can be used to calculate the input magnitude for each of the plurality of digital signals. These input magnitudes can be combined and averaged to determine the first magnitude estimate. Specifically, after detecting these input magnitudes at each time point using any of the algorithms listed above, the first magnitude estimate can be determined by combining several of these input magnitudes together and taking the arithmetic mean of the input magnitudes.

The envelope detection is typically performed using signal filtering, either in hardware or software. To calculate the input magnitude for each of the plurality of digital signals, the envelope detection can be performed with a formula: v=|s|*LPF, where v is the input magnitude, the s is the recorded signal, the LPF stands for a low-pass filter, and * is an operator representing time-convolution.

The Euclidean-norm is the standard $\sqrt{Q^2+I^2}$ that is commonly used for taking the magnitude of complex numbers. In the two-dimensional Euclidean space equipped with the Euclidean-norm, elements in this vector space are usually drawn as arrows in a two-dimensional Cartesian coordinate system starting at the origin (0, 0). The Euclidean norm assigns to each vector the length of its arrow. Because of this, the Euclidean norm is often known as the magnitude. To calculate the input magnitude for each of the plurality of digital signals, the Euclidean-norm can be performed with a formula: $v=\sqrt{Q^2+I^2}$ where v is the input magnitude, Q is quadrature components, and I is in-phase components.

The Hilbert transform is a frequency based approach to finding the low-frequency envelope (i.e., magnitude) of the high-frequency ultrasound signal. To calculate the input magnitude for each of the plurality of digital signals, the Hilbert transform can be performed with a formula:

$$v = s * \frac{1}{\pi t}$$

where v is the input magnitude, s is the recorded signal, and * is an operator representing time-convolution.

Demodulation shifts the high-frequency ultrasound signal down to a lower band where it can be used directly. Demodulation can be based upon time-domain formulation or a frequency-domain formulation. To calculate the input magnitude for each of the plurality of digital signals, the demodulation can be performed with a formula: v=[s·cos(ωt)]*LPF, where v is the input magnitude, s is the recorded signal, and ω is the demodulation frequency. The algorithms determining the input magnitude for each of the plurality of digital signals are not limited to those described herein and can have any other formulas such as replacing the square-root with a logarithm.

As described above, the second magnitude estimate can be obtained by multiplying the first magnitude estimate of the plurality of digital signals and a probability that an actual magnitude of the plurality of digital signals is greater than 0. The equation for the second magnitude estimate can be set as:

$$\hat{v} = \left(\frac{1}{N}\Sigma_i v_i\right)\left(1 - \frac{e^{\frac{1}{N}\Sigma_i -v_i^2/2\sigma^2}}{A}\right),$$

where $\hat{v}$ is the second magnitude estimate, N is a number of samples, $v_i$ is an $i^{th}$ input magnitude, σ is a standard deviation of noise in Gaussian distribution, and A is a constant for a filter aggressiveness.

The $$\frac{1}{N}\Sigma_i v_i$$

in the above equation can represent the first magnitude estimate or the standard magnitude estimate. Here, the first magnitude estimate of the plurality of digital signals can be determined by using any combination of the standard signal acquisition techniques and the algorithms to determine the input magnitude described above. For example, for the plurality of digital signals that is converted with Quadrature sampling, the input magnitudes for each of the plurality of digital signals can be determined using Hilbert transform. After the input magnitudes are determined, the first magnitude estimate of the plurality of digital signals can be calculated by taking the arithmetic mean of the input magnitudes. In another example, for the plurality of digital signals that is converted with Nyquist sampling, the input magnitudes for each of the plurality of digital signals can be determined by envelope detection. After that, the first magnitude estimate of the plurality of digital signals can be determined by taking the arithmetic mean of the input magnitudes. The combinations of the standard signal acquisition techniques and the algorithms for the input magnitudes are not limited to the combinations described above and can have any other combinations.

In another embodiment where the plurality of digital signals is obtained by quadrature sampling and the input Q, I pairs are directly used for the standard magnitude estimate, the second magnitude estimate can be generated using a quadrature specific formula: $\hat{v}=(\sqrt{Q^2+I^2})p(v>0|Q,I)$. This equation can be reduced to:

$$p(v > 0 \mid Q, I) = 1 - \Pi_i \frac{e^{-Q_i^2/2\sigma^2}}{A}\Pi_i \frac{e^{-I_i^2/2\sigma^2}}{A}$$

where σ is the standard deviation of noise in Gaussian distribution, and A is a constant for filter aggressiveness. This reduced equation becomes:

$$\hat{v} = \left(\sqrt{Q^2+I^2}\right)\left(1 - \frac{e^{\Sigma_i -(Q_i^2+I_i^2)/2\sigma^2}}{A}\right),$$

where $\hat{v}$ is the second magnitude estimate, σ is the standard deviation of noise in Gaussian distribution, and A is a constant for a filter aggressiveness. This equation can be suitable for use on envelope data as well as QI or RF data. In this formulation, A, the constant for filter aggressiveness, can be modified to adjust the aggressiveness of the filter.

An ultrasound image generally has detail resolution and contrast resolution. The detail resolution refers to a measure of the minimum spacing of distinguishable point targets. The contrast resolution refers to a measure of how low the acoustic noise levels are relative to the maximum signal level. The contrast resolution determines the ability to distinguish resolvable structures or echogenicity differences between neighboring soft tissue regions. The contrast resolution of an ultrasound image is based upon relative pixel brightness. The image created by the first magnitude estimate (or standard magnitude estimate) can be a standard ultrasound image such as B-Mode ultrasound image. Each of the images created by the first magnitude estimate and the second magnitude estimate respectively has its own contrast resolution. However, the image created with the second magnitude estimate has superior contrast resolution compared to the image created using the first magnitude estimate because the simplified technique described above makes the second magnitude estimate closer to the actual true value. In other words, the simplified technique gets a more accurate estimate of the true pixel value, thereby improving the contrast resolution of the ultrasound image.

Figure 2:
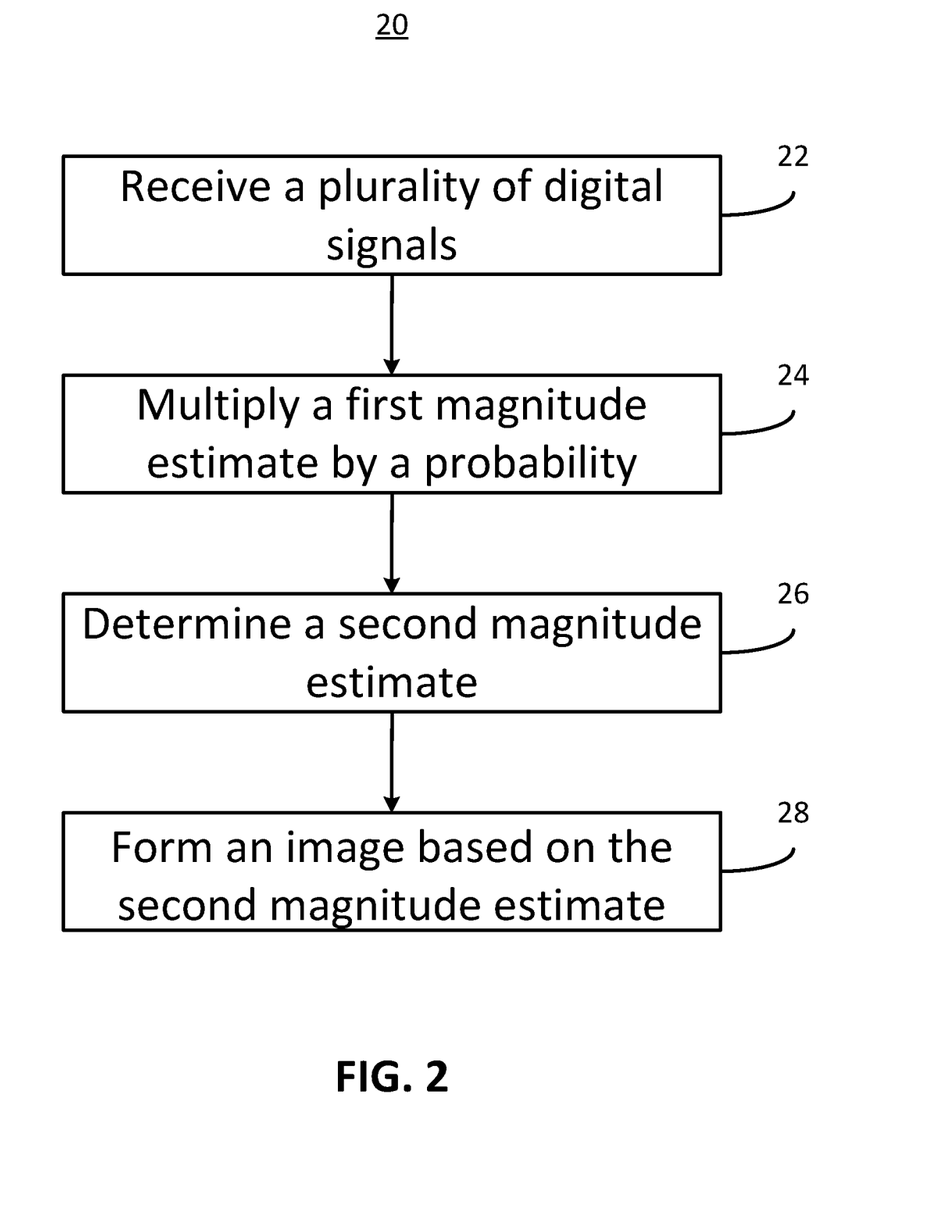
FIG. 2 illustrates a flow diagram of an embodiment of the present invention directed to the imaging process (20) that estimates the magnitude of a signal whose components are corrupted by the presence of noise.

FIG. 2 illustrates an embodiment of imaging process (20) that estimates the magnitude of the plurality of digital signals whose components are corrupted by the presence of noise. The imaging process (20) can be directed to a simplified technique that enhances the contrast resolution of the ultrasound image. For example, at step 22, one or more processors receive a plurality of digital signals that are converted from a scanner with standard signal acquisition techniques. The standard signal acquisition techniques can include Quadrature sampling Nyquist sampling, or the like. The plurality of digital signals is also being correlated to a magnitude (or brightness) of a pixel of a digital image. Upon receiving the plurality of digital signals, the one or more processors can calculate the input magnitudes for each of the plurality of digital signals with different algorithms to determine the first magnitude estimate. The algorithms can include Euclidean-norm, Hilbert transform, envelope detection, demodulation, or the like. It is also noted that the first magnitude estimate of the plurality of digital signals can be determined by combining any of the standard signal acquisition techniques with any of the algorithms to determine the input magnitudes. The combinations of the standard signal acquisition techniques and algorithms are also not limited to the combinations described herein and can have any other combinations.

Upon determining the first magnitude estimate of the plurality of digital signals, at step 24 the second magnitude estimate is determined by multiplying the first magnitude estimate and a probability that an actual magnitude of the plurality of digital signals is greater than 0. For example, the second magnitude estimate can be generated using a formula:

$$\hat{v} = \left(\frac{1}{N}\Sigma_i v_i\right)\left(1 - \frac{e^{\frac{1}{N}\Sigma_i -v_i^2/2\sigma^2}}{A}\right),$$

where $\hat{v}$ is the second magnitude estimate, N is a number of samples, $v_i$ is an $i^{th}$ input magnitude, $\sigma$ is a standard deviation of noise in Gaussian distribution, and A is a constant for a filter aggressiveness. Here, the equation $$\frac{1}{N}\Sigma_i v_i$$

can indicate the first magnitude estimate, which is the standard magnitude estimate of the plurality of digital signals.

Upon determining the second magnitude estimate, at step 28, an ultrasound image with enhanced contrast resolution can be formed based on the second magnitude estimate. Each of the images created by the first and second magnitude estimates can have its own contrast resolution that shows the detectability of resolvable structures on the images. However, because the simplified technique described above makes the second magnitude estimate closer to the actual true value, the image created using the second magnitude estimate has superior contrast resolution compared to the image created using the first magnitude estimate. In other words, the simplified technique improves the contrast resolution of the ultrasound image. This enhanced contrast resolution is based upon relative pixel brightness.

In another embodiment, the simplified technique can be controlled primarily by executable instructions, which can be in the form of software, wherever, or by whatever means such software is stored or accessed. Such executable instructions can reside in a computer readable storage medium and, when executed by a process can cause the processor to effectuate imaging processing operations that is directed to the simplified technique.

For example, the image processing operations include receiving a plurality of digital signals converted from a scanner with standard signal acquisition techniques. The standard signal acquisition techniques can include Quadrature sampling, Nyquist sampling, or the like. The plurality of digital signals is also being correlated to a magnitude (or brightness) of a pixel. The image processing operations can also include calculating the input magnitude for each of the plurality of digital signals with different algorithms to determine the first magnitude estimate. The different algorithms can include Euclidean-norm, Hilbert transform, envelope detection, demodulation, or the like. The different algorithms can be combined with any of sampling techniques to generate the first magnitude of the plurality of digital signals. For example, the plurality of digital signals generated by Nyquist sampling is calculated with the Hilbert transform to detect the input magnitudes for each of the plurality of digital signals. After detecting the input magnitudes, the first magnitude estimate can be determined by averaging the input magnitudes as described above. The combinations of the standard signal acquisition techniques and algorithms are also not limited to the combinations described herein and can have any other combinations.

The image processing operations can include generating the second magnitude estimate by multiplying the first magnitude estimate and a probability that an actual magnitude of the plurality of digital signals is greater than 0. Upon determining the second magnitude estimate, an ultrasound image can be formed based on the second magnitude estimate. Each of the images created by the first and second magnitude estimates can have its own contrast resolution. However, because the simplified technique described above improves the second magnitude estimate closer to the actual true value, the image created using the second magnitude estimate has superior contrast resolution compared to the image created using the first magnitude estimate.

Combined Technique

Referring back to FIG. 1, the imaging system (10) can be directed to a combined technique for its contrast resolution enhancement technique (15). Using the combined technique, the imaging system (10) can also estimate the magnitude of a signal whose components are corrupted by the presence of noise. For example, similar to the simplified technique described above, the imaging system (10) can include a transducer (12), a scanner (14), a signal processing unit (16) that is implementing the combined technique, and a display unit (18). The scanner (14), operatively connected to the transducer (12), can convert a plurality of analog signals received from the transducer (12) into a plurality of digital signals.

The signal processing unit (16), operatively connected to the scanner (14), can receive the plurality of digital signals from the scanner (14) to estimate the magnitude of the plurality of digital signals. The plurality of digital signals can be sampled with standard signal acquisition techniques such as Quadrature sampling, Nyquist sampling, or the like. The plurality of digital signals is also being correlated to a magnitude of a pixel. The signal processing unit (16) can determine a first, second, third, and fourth magnitude estimates. The first magnitude estimate, which is being indicative of the standard magnitude estimate, can be determined by taking the arithmetic mean of input magnitudes. These input magnitudes are determined by the algorithms such as Euclidean-norm, Hilbert transform, envelope detection, demodulation, or the like. It is noted that the first magnitude estimate of the plurality of digital signals can be determined by using any combination of the standard signal acquisition techniques and the algorithms to determine the input magnitudes as described above. The combinations of the standard signal acquisition techniques and algorithms are not limited to the combinations described herein and can have any other combinations.

The second magnitude estimate, which is an implementation of an unbiased technique, can be determined by subtracting a standard deviation of noise from the first magnitude estimate. In other words, it attempts to subtract off the noise terms from the standard magnitude estimate. The third magnitude estimate can be determined by multiplying the first magnitude estimate and a probability that an actual magnitude of the plurality of digital signals is greater than 0. The third magnitude estimate is the implementation of the simplified technique as described above. The fourth magnitude estimate can be determined by simply averaging the second and third magnitude estimates.

Upon determining the second, third, and fourth magnitude estimates, the signal processing unit (16) can select a reliable magnitude estimate based on each of the reliabilities in determining the second, third, and fourth magnitude estimates. For example, the signal processing unit (16) can compare the error rates for true magnitude values for each technique that has been used in determining the second, third, and fourth magnitude estimates. Based on the result of comparison, the signal processing unit (16) can select the reliable magnitude estimate and form at least one portion of an image based upon the reliable magnitude estimate. The reliable magnitude estimate can be changed depending on the scanning region and the reliability (i.e. error rates) of each magnitude estimate. For example, if the error rate for true magnitude values for the third magnitude estimate is higher than that of the fourth magnitude estimate, the fourth magnitude is determined to be more reliable than the third magnitude and the signal processing unit (16) selects the fourth magnitude estimate as its reliable magnitude estimate. Then, the signal processing unit (16) can form the portion of image, for example pixels on the image, with the fourth magnitude estimate. The display unit (18), connected to the signal processing unit (16), can display the portion or all of image based on the selected reliable magnitude estimate. The image formed based on the reliable magnitude estimate also has enhanced contrast resolution compared to the images separately formed based upon each of the second, third, and fourth magnitude estimates.

The second magnitude estimate in the combined technique can be determined using a formula:

$$\hat{v} = \text{Real}\left\{\sqrt{\frac{1}{N}\Sigma_i v_i^2 - 2\sigma^2}\right\}$$

where $\hat{v}$ is the second magnitude estimate, N is a number of samples, $v_i$ is an $v^i$ input magnitude, and $\sigma$ is a standard deviation of noise in Gaussian distribution. The second magnitude estimate is a more direct implementation to calculate the magnitude estimate by subtracting off the noise from the standard magnitude estimate. For example, the standard magnitude estimate for B-Mode ultrasound image is generated using an equation: $\text{Magnitude}^2=(Q+\epsilon_Q)^2+(I+\epsilon_I)^2=(Q^2+I^2)+2Q\epsilon_Q+2I\epsilon_I+\epsilon_Q^2+\epsilon_I^2$, where Q are true quadrature components, I are true in-phase components, and $\epsilon$ is the added noise term to the true Q and I values. From this equation, it can be assumed that Q and I are small so that the multiplicative error goes to zero and the standard deviation of the noise term is subtracted off: $\hat{v}^2=(Q^2+I^2)+\epsilon_Q^2+\epsilon_I^2-2\sigma^2$. Then working with the actual noise corrupted data, the possible magnitude estimate can be: $\hat{v}=\sqrt{(Q+\epsilon_Q)^2+(I+\epsilon_I)^2-2\sigma^2}$. Although this magnitude estimate is unbiased, it can give imaginary values when Q and I are small. These imaginary values are easily dealt with by setting any purely imaginary numbers to zero, that is, by taking only the real component. However, when the number of observations is small, this can cause zeros in the resulting image which are both inaccurate and visually distracting. An averaging step can be performed either before the subtraction step or after the square root. Averaging before the subtraction step is more numerically stable, but averaging before the square root step is more accurate.

The third magnitude estimate in the combined technique can be obtained by multiplying the first magnitude estimate of the plurality of digital signals and a probability that an actual magnitude of the plurality of digital signals is greater than 0. The third magnitude estimate can be generated using a formula:

$$\hat{v} = \left(\frac{1}{N}\Sigma_i v_i\right)\left(1 - \frac{e^{\frac{1}{N}\Sigma_i -v_i^2/2\sigma^2}}{A}\right),$$

where $\hat{v}$ is the third magnitude estimate, N is a number of samples, $v_i$ is an $i^{th}$ input magnitude, $\sigma$ is a standard deviation of noise in Gaussian distribution, and A is a constant for a filter aggressiveness. Here, the equation, $$\frac{1}{N}\Sigma_i v_i,$$

can represent the first magnitude estimate, which is the standard magnitude estimate.

The fourth magnitude estimate can be determined by averaging the second magnitude and third magnitude estimates. When the second and third magnitude estimates are averaged, they can be combined with arbitrary weights or calculated weights. The arbitrary weight can be determined by a technician who is operating the imaging system (10). The calculated weights can be determined based on error rates of techniques for true magnitude values. For example, a technician operating the imaging system (10) may combine ⅔ of the third magnitude estimate and ⅓ of the second magnitude estimate (i.e ⅔ * Simplified technique +⅓* Unbiased technique) in order to calculate the fourth magnitude estimate by averaging the second and third magnitude estimates. With respect to the calculated weights, the weights can be calculated before combining the second and third magnitude estimates based on their error rates. For example, in a given region, the simplified technique produces 0.1 error rate and the unbiased technique produces 0.9 error rate. This means that, in the given region, the simplified technique has a 90% accuracy rate and the unbiased technique has a 10% accuracy rate and 90% of the third magnitude estimate (simplified technique) and 10% of the second magnitude estimate (unbiased technique) can be combined to calculate the fourth magnitude estimate (i.e. 0.9*Simplified technique+0.1*Unbiased technique).

The image formed based on the reliable magnitude estimate has detail resolution and contrast resolution. As described above, the detail resolution refers to a measure of the minimum spacing of distinguishable point targets and the contrast resolution refers a measure of how low the acoustic noise levels are. The contrast resolution determines the ability to distinguish resolvable structures or echogenicity differences between neighboring soft tissue regions. The contrast resolution of the image based on the reliable magnitude is based upon relative pixel brightness. Each of the images created by the first, second, third, and fourth magnitude estimate has its own contrast resolution. However, the image created with the reliable magnitude estimate can have superior contrast resolution compared to each of the images created by the first, second, third, and fourth magnitude estimate because the combined technique described above can compare reliabilities of each technique and select the most reliable magnitude estimate to form the image of the region. In other words, the combined technique can utilize the magnitude estimates with the lowest error rates for true magnitude values to form a portion of image among the standard, biased, and simplified techniques to determine the magnitude estimate.

Figure 3:
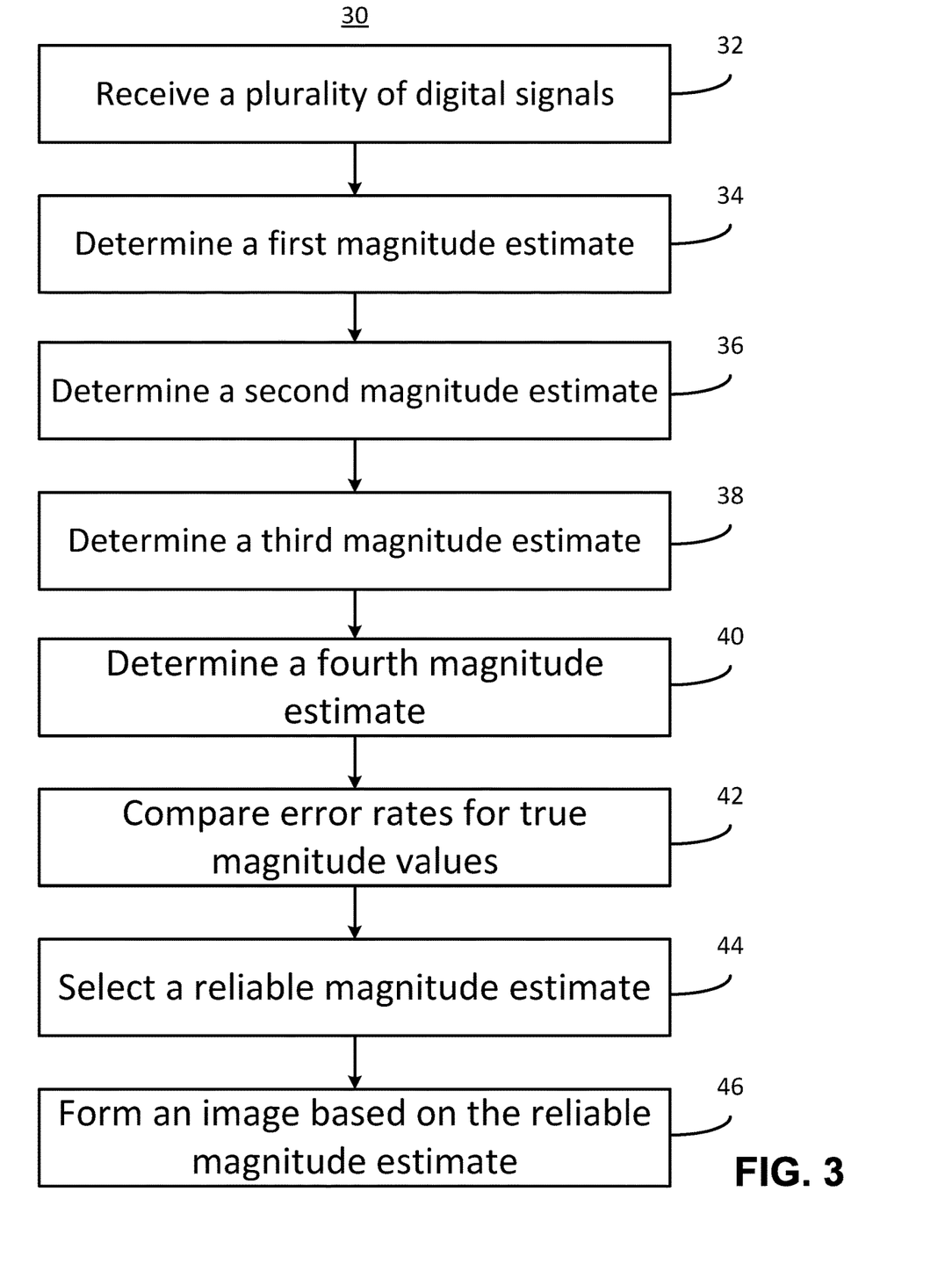
FIG. 3 illustrates a flow diagram of an embodiment of the present invention directed to the imaging process (30) that estimates the magnitude of a signal whose components are corrupted by the presence of noise.

FIG. 3 illustrates an embodiment of imaging process (30) that estimates the magnitude of the plurality of digital signals whose components are corrupted by the presence of noise based on error rates for true magnitude values. The imaging process (30) can be directed to the combined technique. For example, at step 32, one or more processors receive a plurality of digital signals that are converted from a scanner with standard signal acquisition techniques. The standard signal acquisition techniques can include Quadrature sampling, Nyquist sampling, or the like. The plurality of digital signals is also being correlated to a magnitude (or brightness) of a pixel of a digital image. With the plurality of digital signals, the one or more processor can determine a first, second, third, and fourth magnitude estimates. At step 34, the first magnitude estimate, which is being indicative of the stand magnitude estimate, can be determined by taking the arithmetic mean of input magnitudes. These input magnitudes are detected by the algorithms such as Euclidean-norm, Hilbert transform, envelope detection, demodulation, or the like. It is noted that the first magnitude estimate can be determined by using any combination of the standard signal acquisition techniques and the algorithms to determine the input magnitude as described above. The combinations of the standard signal acquisition techniques and algorithms are not limited to the combinations described herein and can have any other combinations At step 36, the second magnitude estimate, which is an implementation of an unbiased technique, can be determined by subtracting a standard deviation of noise from the first magnitude estimate. In other words, the noise terms of the standard deviation is subtracted off from the first magnitude estimate. The second magnitude estimate can be also determined using a formula:

$$\hat{v} = \text{Real}\left\{\sqrt{\frac{1}{N}\Sigma_i v_i^2 - 2\sigma^2}\right\}$$

where $\hat{v}$ is the second magnitude estimate, N is a number of samples, $v_i$ is an $i^{th}$ input magnitude, and $\sigma$ is a standard deviation of noise in Gaussian distribution.

At step 38, the third magnitude estimate can be determined by multiplying the first magnitude estimate and a probability that an actual magnitude of the plurality of digital signals is greater than 0. The third magnitude estimate is the implementation of the simplified technique as described above. The third magnitude estimate can be also generated using a formula:

$$\hat{v} = \left(\frac{1}{N}\sum_i v_i\right)\left(1 - \frac{e^{\frac{1}{N}\sum_i -v_i^2/2\sigma^2}}{A}\right),$$

where $\hat{v}$ is the third magnitude estimate, N is a number of samples, $v_i$ is an $i^{th}$ input magnitude, $\sigma$ is a standard deviation of noise in Gaussian distribution, and A is a constant for a filter aggressiveness. The equation, $$\frac{1}{N}\sum_i v_i,$$

can indicate the first magnitude estimate, which is the standard magnitude estimate.

At step 40, the fourth magnitude estimate can be determined by averaging the second and third magnitude estimates. When the second and third magnitude estimates are averaged, they can be combined using arbitrary weights or calculated weights. The arbitrary weight can be determined by a technician who is operating the imaging system (10). The calculated weights can be determined based on error rates of techniques for true magnitude values.

Upon determining the second, third, and fourth magnitude estimates, a reliable magnitude estimate can be selected, at step 44, among the second, third, and fourth magnitude estimates by comparing, at step 42, the reliabilities of the techniques in determining the second, third, and fourth magnitude estimates. For example, the one or more processors can compare the error rates for true magnitude values for each technique that has been used in determining the second, third, and fourth magnitude estimates. Based on the result of comparison, the one or more processors can select the reliable magnitude estimate and form at least one portion of an image based upon the reliable magnitude estimate. The reliable magnitude estimate can be changed depending on the scanning region and the reliabilities of the techniques to determine the magnitude estimate. For example, if the error rate for true magnitude values for the third magnitude estimate is higher than that of the fourth magnitude estimate, the fourth magnitude is determined to be more reliable than the third magnitude and the fourth magnitude estimate is selected as its reliable magnitude estimate to form the portion of the image, for example, pixels on the digital image.

Results

Figure 4:
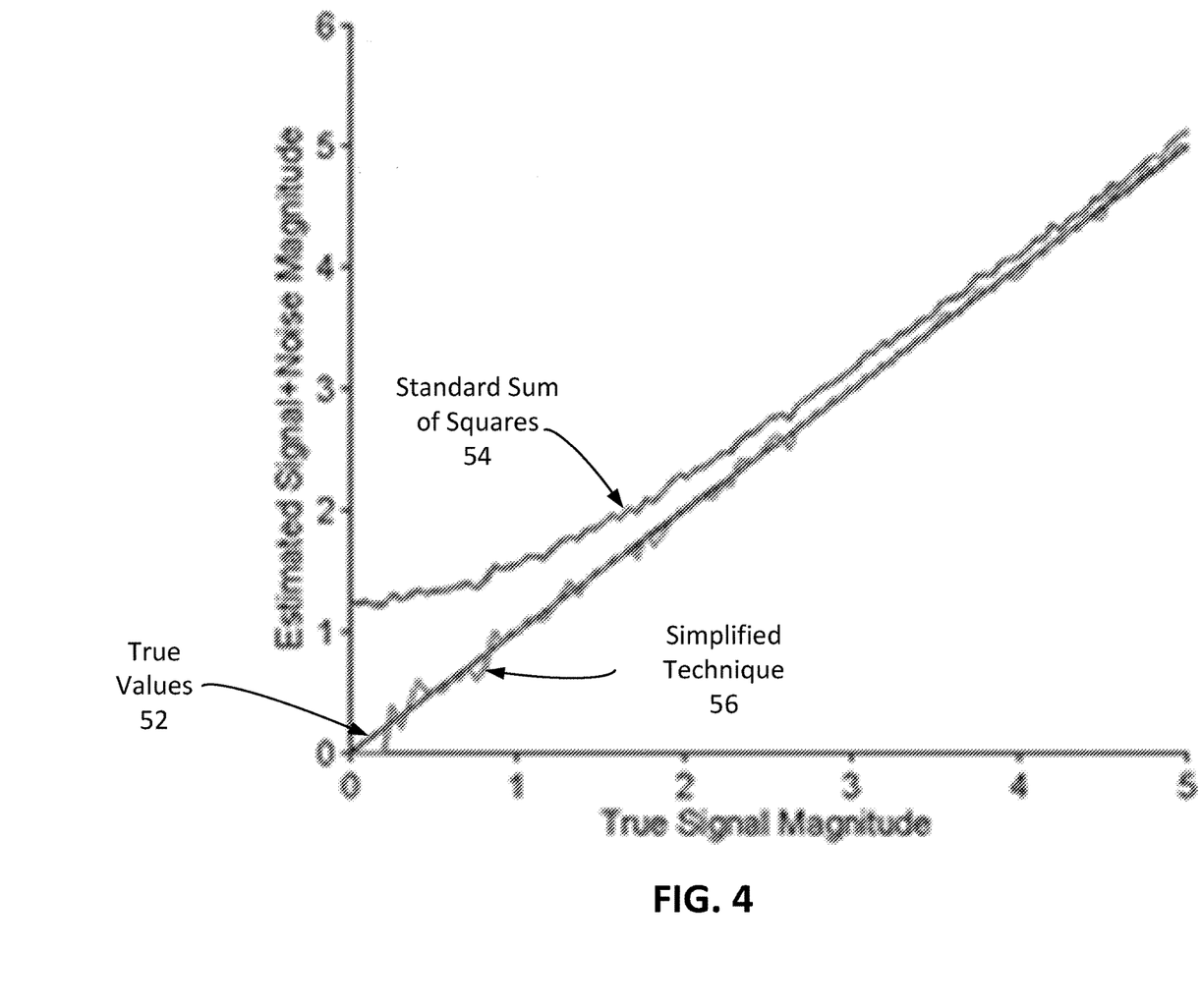
FIG. 4 is a graph illustrating simulated results for estimating signal magnitude (Brightness) with random phase and white Gaussian noise.

FIG. 4 is a graph illustrating simulated results for estimating signal magnitude (Brightness) with random phase and white Gaussian noise. Specifically, FIG. 4 shows the results of a simulation in which 1000 Q, I pairs of a certain magnitude with phase uniformly distributed between –pi and pi were generated. White Gaussian noise with zero mean and a standard deviation of 1 was added to these values.

Both the magnitude estimate by the standard sum of squares (54) and the magnitude estimate by the simplified technique (56) as described above were performed. This was repeated for 100 magnitude values. It is noticed that for small True Signal Magnitude values, the estimated value by the standard sum of squares (54) is higher with a smaller slope. This smaller slope indicates less of a difference between similar values. Further, the contrast (or difference) between values at opposite ends of the scale in FIG. 4 would be 5 for the true signal magnitude, but about 3.8 for the estimated value by the standard sum of squares (54).

Figure 5A:
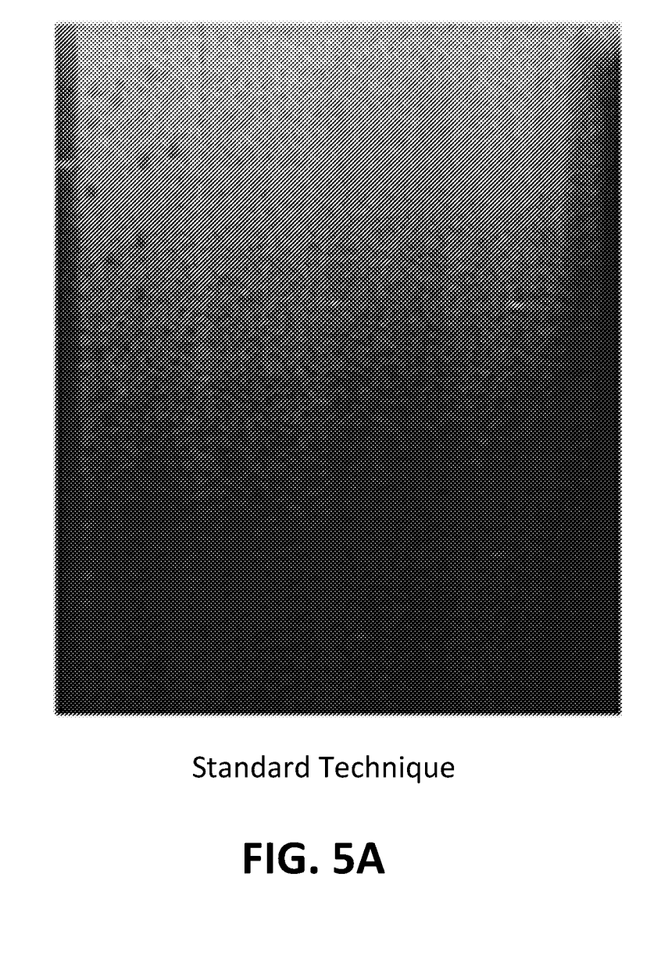
FIG. 5A provides a high frequency ultrasound (HFUS) phantom image under standard technique.
Figure 5B:
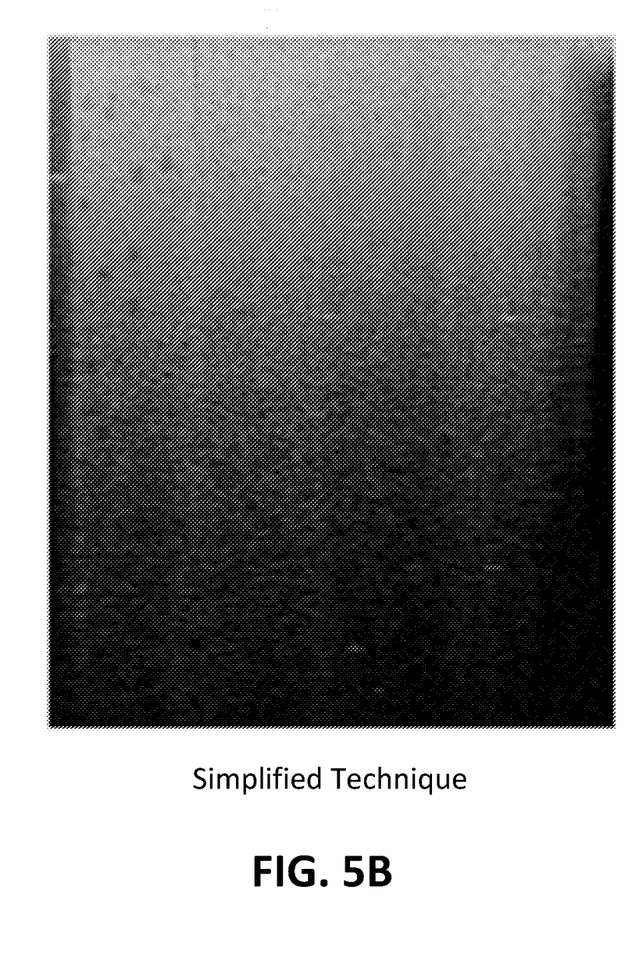
FIG. 5B provides an ultrasound image illustrating the results of applying the imaging process (20) illustrated in FIG. 2 (simplified technique) to the HFUS phantom image shown in FIG. 5A.

FIG. 5A illustrates a high frequency ultrasound (HFUS) phantom image generated by the standard technique. FIG. 5B illustrates an ultrasound image with improved contrast resolution generated by the simplified technique. In FIG. 5B, the simplified technique described above is applied to the HFUS phantom image shown in FIG. 5A. As shown in the FIG. 5B, the contrast is improved for the deeper, low-signal regions of the image. For example, FIG. 5B has noticeably darker portions of the image than FIG. 5A has, particularly near the bottom of both images.

Figure 6A:
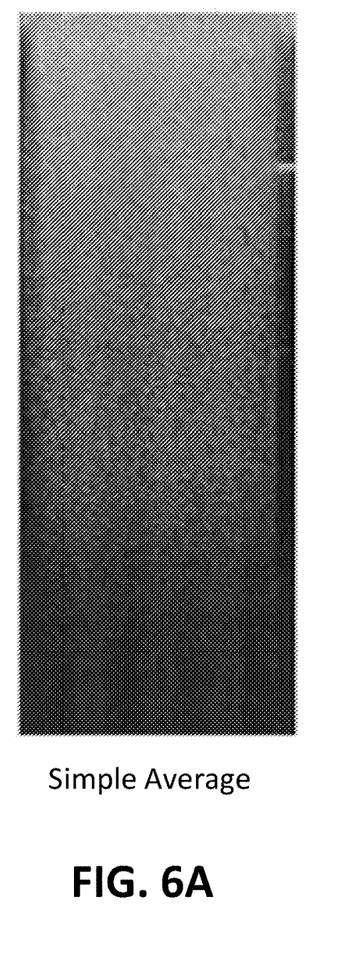
Figure 6B:
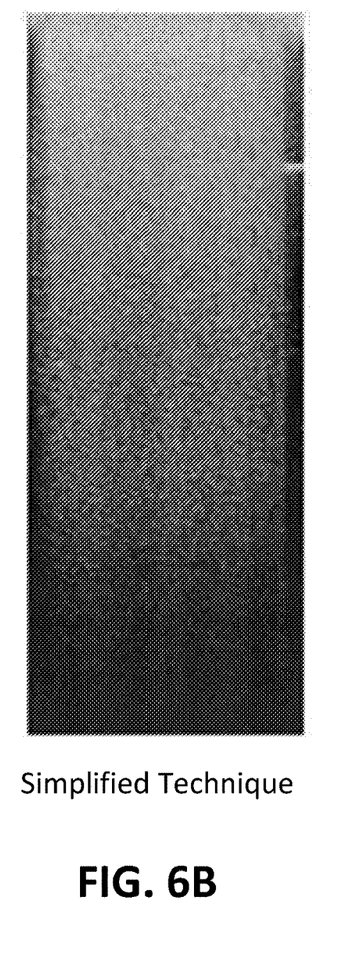
Figure 6C:
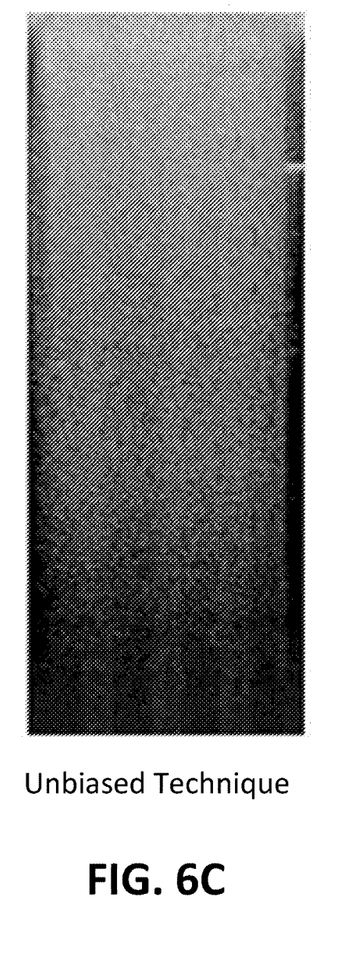
Figure 6D:
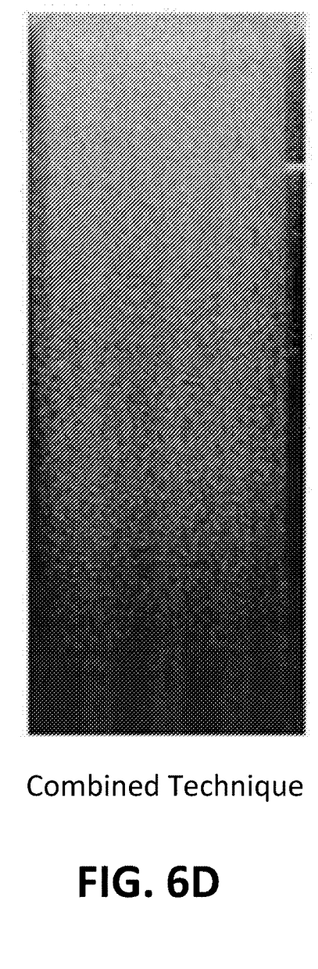

FIGS. 6A-D provide ultrasound images illustrating the results of applying different magnitude estimate techniques to a HFUS phantom image. FIGS. 6A-D show the application of the more practical implementations of the technique to a HFUS phantom image. FIG. 6A is an ultrasound image generated by simple averaging, which refers to the arithmetic mean of standard magnitude estimates. FIGS. 6B-D are ultrasound images generated by the simplified, unbiased, and combined techniques respectively as described above. Similar to FIG. 5B, there is improved contrast resolution, particularly for deep areas. FIG. 6A has noticeably worse contrast resolution compared to the other images in FIGS. 6B-D. Each of the other images in FIGS. 6B-D shows varying levels of contrast improvements and some artefact in FIG. 6C, as described above.

Figure 7A:
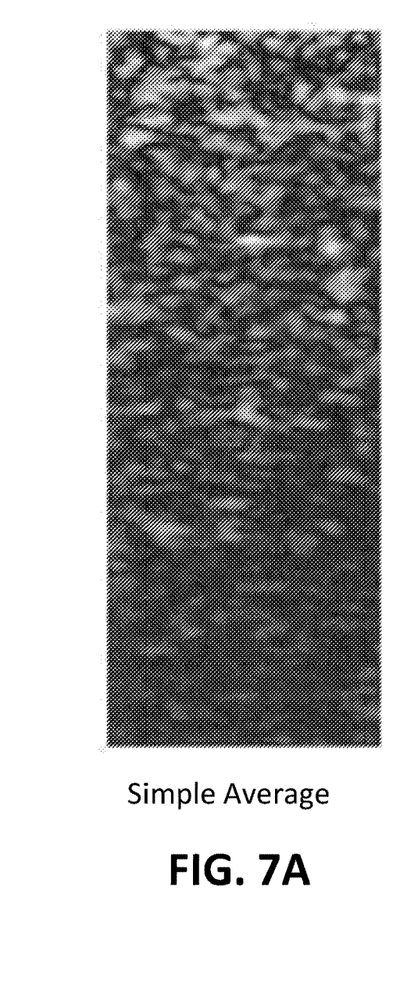
Figure 7B:
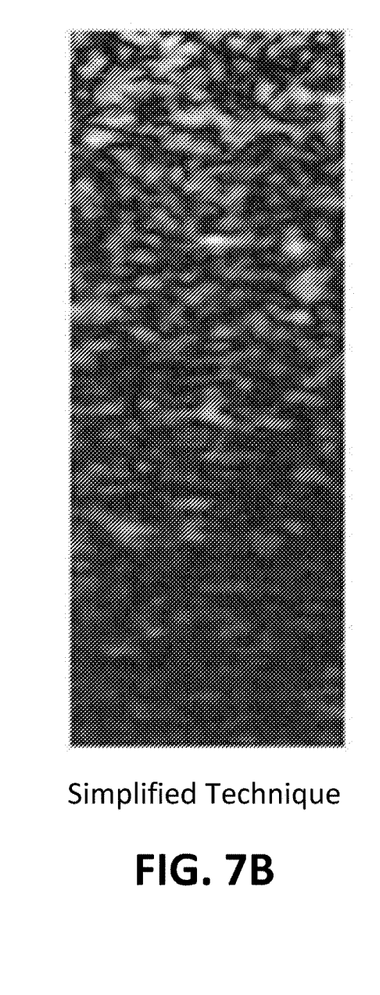
Figure 7C:
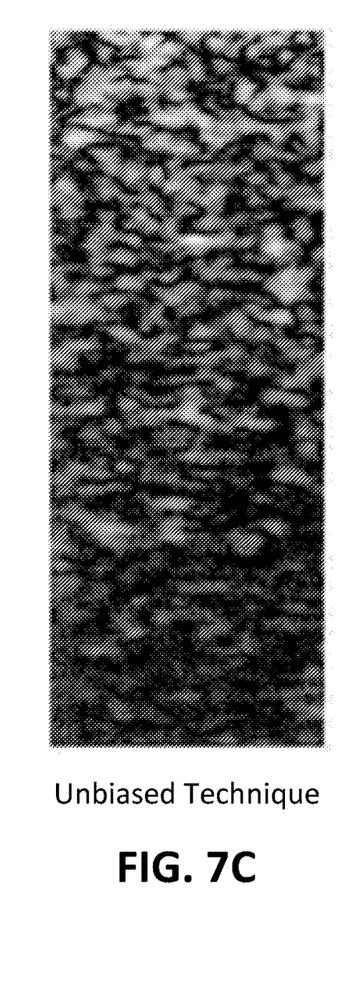
Figure 7D:
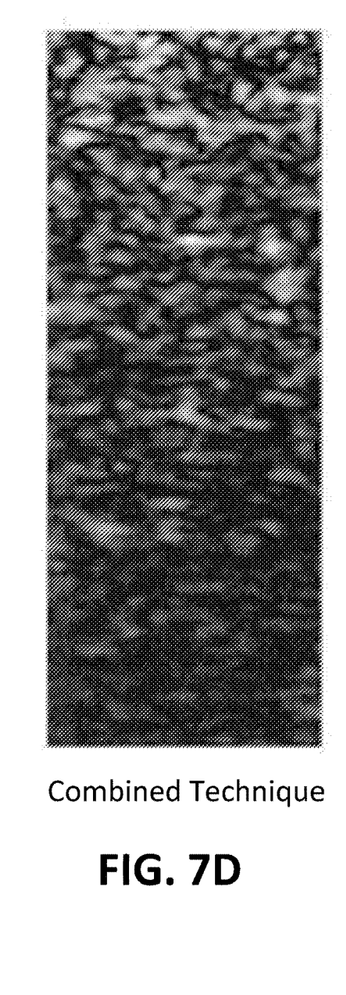

FIGS. 7A-D provide another set of ultrasound images showing the results of applying different magnitude estimate techniques to a HFUS phantom image. FIGS. 7A-D also shows the application of the more practical implementations of the technique to a HFUS phantom image. FIG. 7A is an ultrasound image generated by simple averaging. FIGS. 7B-D are ultrasound images generated by the simplified, unbiased, and combined techniques respectively as described above. Similar to FIG. 6, there is improved contrast resolution, particularly for deep areas. For example, this view makes the artefact in FIG. 7C more noticeable, as well as the differences in the dark areas of the images. FIGS. 7B-D have darker dark areas compared to FIG. 7A, thereby indicating both improved contrast and contrast resolution.

Figure 8:
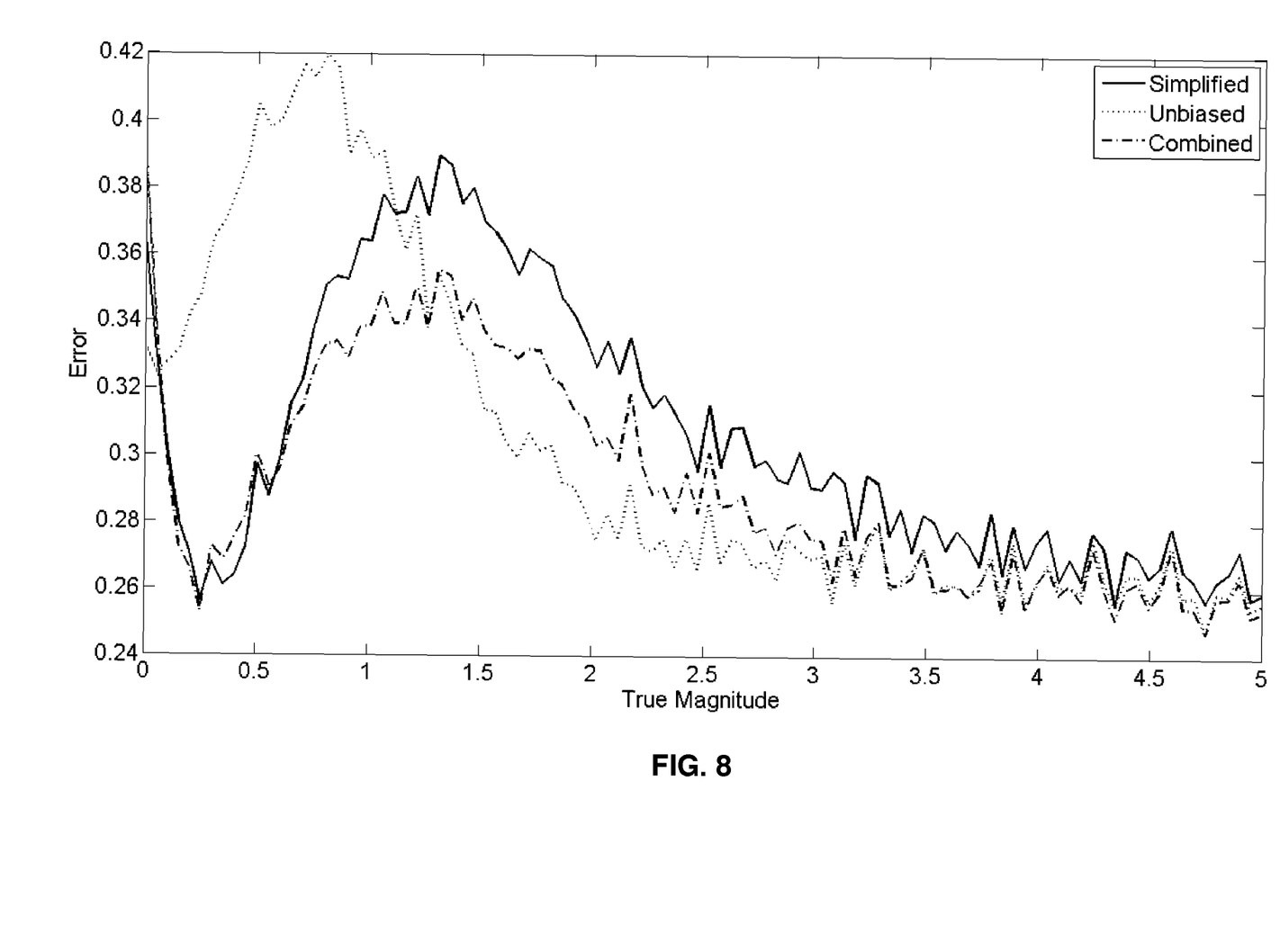
FIG. 8 is a graph illustrating average errors for each true magnitude value in implementing the simplified, unbiased, and combined techniques.

FIG. 8 presents average error rates for each true magnitude value given sets of 10 observations for the simplified, unbiased, and combined techniques describe above. These error rates depend on the number of observations as well as the true magnitude and noise level. As the number of observations becomes very large, the unbiased technique outperforms the simplified and combined techniques. However, when the number of observations is limited as in the practical implementation, FIG. 8 shows that the combined technique can provide the lowest error rate over some range of true magnitude and noise level (i.e. a more efficient estimator). The regions where each technique is reliable can be seen as the area where the error rate of one technique is lower than that of the other technique. For example, between about $0.1*\sigma$ and about $1.25*\sigma$ on the true magnitude axis, the simplified and combined techniques are more reliable than the unbiased techniques. It is also noted that these unbiased, simplified, and combined techniques are noticeably more reliable than typical standard magnitude estimate approximately below $5*\sigma$ on the true magnitude axis.

In another embodiment, the contrast resolution enhancement techniques can improve contrast resolution in ultrasound images at the expense of frame rate, that is, speed of image acquisition due to temporal averaging. This can be useful in a number of scenarios, for example, to provide clearer images of a subject that is relatively still, to provide increased accuracy in material analysis, to improve the contrast resolution of persistence images, and/or to improve composite ultrasound images created using the contrast resolution enhancement techniques that average data such as spatial compounding or frequency compounding.

It is understood that any or all of the systems, methods and processes described herein may be embodied in the form of computer executable instructions (i.e., program code) stored on a computer-readable storage medium which instructions, when executed by a machine, such as a ultrasound imaging system, computer, medical device, or the like, perform and/or implement the systems, methods and processes described herein. Specifically, any of the steps, operations or functions described above can be implemented in the form of such computer executable instructions. Computer readable storage media include both volatile and nonvolatile, removable and non-removable media implemented in any method or technology for storage of information, but such computer readable storage media do not includes signals. Computer readable storage media include, but are not limited to, RAM, ROM, EEPROM, flash memory or other memory technology, CDROM, digital versatile disks (DVD) or other optical disk storage, magnetic cassettes, magnetic tape, magnetic disk storage or other magnetic storage devices, or any other physical medium which can be used to store the desired information and which can be accessed by a computer.

It is also to be understood that while the invention has been described in conjunction with the preferred specific embodiments thereof, that the foregoing description and the examples that follow are intended to illustrate and not limit the scope of the invention. It will be understood by those skilled in the art that various changes can be made and equivalents can be substituted without departing from the scope of the invention, and further that other aspects, advantages and modifications will be apparent to those skilled in the art to which the invention pertains. For example, the contrast resolution techniques described herein can be used as an integral part of the signal path on an ultrasound device for image generation or material analysis, as a post-processing unit attached to an ultrasound device, or as a software package to enhance previously saved ultrasound data. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. An ultrasound imaging system comprising:
a transducer;
a scanner, operatively connected to the transducer, for converting a plurality of analog signals from the transducer to a plurality of digital signals;
a signal processing unit, operatively connected to the scanner, the signal processing unit configured to:
   receive the plurality of digital signals, the plurality of digital signals being correlated to a magnitude of a pixel;
   determine a first magnitude estimate of the plurality of digital signals, the first magnitude estimate being indicative of a standard magnitude estimate;
   determine a second magnitude estimate by subtracting a standard deviation of noise from the first magnitude estimate;
   determine a third magnitude estimate by multiplying the first magnitude estimate and a probability that an actual magnitude of the plurality of digital signals is greater than 0;
   determine a fourth magnitude estimate by averaging the second magnitude estimate and the third magnitude estimate
   compare error rates for true magnitude values in determining the second, third, and fourth magnitude estimates to select a reliable magnitude estimate; and
   form at least one portion of an image based upon the reliable magnitude estimate thereby providing an enhanced contrast resolution of the image compared to an image created by the first magnitude estimate
and a display unit, connected to the signal processing unit, showing the image;
wherein the first magnitude estimate of the plurality of digital signals is generated using the formula:

$$\hat{v} = \frac{1}{N}\sum_i v_i$$

wherein
$\hat{v}$ is the first magnitude estimate,
N is a number of samples, and
$v_i$ is the $i^{th}$ input magnitude;
wherein the second magnitude estimate is generated using a formula:

$$\hat{v} = \text{Real}\left\{\sqrt{\frac{1}{N}\sum_i v_i^2 - 2\sigma^2}\right\}$$

wherein,
$\hat{v}$ is the second magnitude estimate,
N is a number of samples,
$v_i$ is an $i^{th}$ input magnitude, and
$\sigma$ is a standard deviation of noise in Gaussian distribution;
wherein the third magnitude estimate is generated using either one of a formula:

$$\hat{v} = \left(\frac{1}{N}\sum_i v_i\right)\left(1 - \frac{e^{\frac{1}{N}\sum_i -v_i^2/2\sigma^2}}{A}\right)$$

or a quadrature specific formula:

$$\hat{v} = \left(\sqrt{Q^2 + I^2}\right)\left(1 - \frac{e^{\sum_i -(Q_i^2 + I_i^2)/2\sigma^2}}{A}\right)$$

wherein,
$\hat{v}$ is the third magnitude estimate,
N is a number of samples,
$v_i$ is an $i^{th}$ input magnitude, and
$\sigma$ is a standard deviation of noise in Gaussian distribution;
A is a constant for a filter aggressiveness,
Q is quadrature components, and
I is in phase components; and
wherein the probability is reduced to:

$$p(v > 0 \mid Q, I) = 1 - \prod_i \frac{e^{-Q_i^2/2\sigma^2}}{A} \prod_i \frac{e^{-I_i^2/2\sigma^2}}{A}$$

wherein
$\sigma$ is a standard deviation of noise in Gaussian distribution, and
A is a constant for a filter aggressiveness.

2. The imaging system of claim 1, wherein the demodulation is a time-domain demodulation formulation, a frequency domain demodulation formulation, or a combination thereof.

3. A method for forming an ultrasound image comprising:
receiving, at one or more processors, a plurality of digital signals, the plurality of digital signals being correlated to a magnitude of a pixel;
determining, via the one or more processors, a first magnitude estimate of the plurality of digital signals, the first magnitude estimate being indicative of a standard magnitude estimate;
determining, via the one or more processors, a second magnitude estimate by subtracting a standard deviation of noise from the first magnitude estimate;
determining, via the one or more processors, a third magnitude estimate by multiplying the first magnitude estimate and a probability that an actual magnitude of the plurality of digital signals is greater than 0;
determining, via the one or more processors, a fourth magnitude estimate by averaging the second magnitude estimate and the third magnitude estimate;
comparing error rates for true magnitude values in determining the second, third, and fourth magnitude estimates to select a reliable magnitude estimate;
forming at least one portion of an image based upon the reliable magnitude estimate thereby providing an enhanced contrast resolution of the image compared to an image created by the first magnitude estimate; and
wherein the first magnitude estimate of the plurality of digital signals is generated using a formula:

$$\hat{v} = \frac{1}{N}\sum_i v_i$$

wherein,
$\hat{v}$ is the first magnitude estimate,

N is a number of samples, and
$v_i$ is an $i^{th}$ input magnitude,
wherein the second magnitude estimate is generated using a formula:

$$\hat{v} = \text{Real}\left\{\sqrt{\frac{1}{N}\sum_i v_i^2 - 2\sigma^2}\right\}$$

wherein
$\hat{v}$ is the second magnitude estimate,
N is a number of samples,
$v_i$ is an $i^{th}$ input magnitude, and
σ is a standard deviation of noise in Gaussian distribution;
wherein the third magnitude estimate is generated using either one of a formula:

$$\hat{v} = \left(\frac{1}{N}\sum_i v_i\right)\left(1 - \frac{e^{\frac{1}{N}\sum_i -v_i^2/2\sigma^2}}{A}\right)$$

or a quadrature specific formula:

$$\hat{v} = \left(\sqrt{Q^2 + I^2}\right)\left(1 - \frac{e^{\sum_i -(Q_i^2+I_i^2)/2\sigma^2}}{A}\right)$$

wherein
$\hat{v}$ is the third magnitude estimate,
N is a number of samples,
$v_i$ is an $i^{th}$ input magnitude, and
σ is a standard deviation of noise in Gaussian distribution,
A is a constant for a filter aggressiveness,
Q is quadrature components, and
I is in phase components; and
wherein the probability is reduced to:

$$p(v > 0 \mid Q, I) = 1 - \prod_i \frac{e^{-Q_i^2/2\sigma^2}}{A} \prod_i \frac{e^{-I_i^2/2\sigma^2}}{A}$$

wherein,
σ is a standard deviation of noise in Gaussian distribution, and
A is a constant for a filter aggressiveness.

4. The imaging system of claim 1, wherein the second magnitude estimate and the third magnitude estimate are combined using arbitrary weights when averaging the second magnitude estimate and the third magnitude estimate to determine the fourth magnitude estimate.

5. The imaging system of claim 1, wherein the second magnitude estimate and the third magnitude estimate are combined using calculated weights when averaging the second magnitude estimate and the third magnitude estimate to determine the fourth magnitude estimate.

6. The imaging system of claim 5, wherein the calculated weights are determined based on error rates for true magnitude values.

7. The Imaging system of claim 1, wherein the plurality of digital signals is generated by a technique comprising a Quadrature sampling, a Nyquist sampling, or any combination thereof.

8. The imaging system of claim 1, wherein an input magnitude for each of the plurality of digital signals is determined by an algorithm comprising Euclidean-norm, Hilbert transform, envelope detection, demodulation, or any combination thereof.

* * * * *